United States Patent [19]

McLoughlin, Thomas J.

[11] Patent Number: 4,713,330

[45] Date of Patent: Dec. 15, 1987

[54] VISUAL BIOASSAY FOR RHIZOBIUM COMPETITION VARIANTS

[75] Inventor: McLoughlin, Thomas J., Cottage Grove, Wis.

[73] Assignee: Lubrizol Genetics, Inc., Wickliffe, Ohio

[21] Appl. No.: 812,251

[22] Filed: Dec. 23, 1985

[51] Int. Cl.$^4$ ............................................. C12Q 1/04
[52] U.S. Cl. ........................................ 435/34; 435/29
[58] Field of Search ............................ 435/29, 34, 37

[56] References Cited

PUBLICATIONS

Sylvester-Bradley et al—Chem. Abst., vol. 100, (1984), p. 67287a.
Means et al—Soil Science Soc. Proc., vol. 25, pp. 105–108.
Dowling, D. N. et al., (1985), in *Nitrogen Fixation Research Progress*, eds.
Evans, H. J. et al., ISBN 90-242-3255-7, p. 141.
Eaglesham, A. R. J. et al., (1982), Appl. Environ. Microbiol., 44:611–618.
Berestetskii, O. A. et al., (1983), Mikrobiologiya, (Moscow), 52:651–657.
Brewin, N. J. et al., (1983), J. Gen. Microbiol. 129:2973–2977.
Diatloff, A. and Brockwell, J., (1974), Austral. J. Exp. Agric. Husb., 16:514–521.

*Primary Examiner*—Sam Rosen
*Attorney, Agent, or Firm*—Greenlee and Associates

[57] ABSTRACT

A simple, generalized method is disclosed for screening a collection of Rhizobium or Bradyrhizobium strains for variants which, in nodulation, have competative abilities above or below a particular experimentally-set criterion. This method involves mixing a Fix$^+$ test strain with a Fix$^-$ reference strain, followed by inoculation of a legume plant with the mixture and observation of the inoculated plant's foliage for symptoms of nitrogen sufficiency (green foliage) or nitrogen deficiency (yellow foliage). The method is exemplified by the identification of mutants of both *R. fredii* and *B. japonicum* which are phenotypically Comp$^-$ on soybeans (*Glycine max*).

22 Claims, No Drawings

VISUAL BIOASSAY FOR RHIZOBIUM COMPETITION VARIANTS

FIELD

The present invention is in the fields of genetic engineering and plant husbandry and in particular provides a means for identification of genetically altered Rhizobium cells that have differing abilities to compete in nodulation with other Rhizobium cells.

BACKGROUND

Assessment of Rhizobium strains for competitive ability is well known to the art (e.g. Brewin NJ et al. (1983) J. Gen. Microbiol. 129:2973-2977). Effective and ineffective Rhizobium strains have been assessed for symbiotic and competitive abilities by measures such as nodulation, foliage dry weight, foliage nitrogen content, strain recovery from nodules, and the like (Diatloff A and Brockwell J (1974) Austral. J. Exp. Agric. Animal Husb. 16:514-521; Berestetskii OA et al. (1983) Mikrobiologiya (Moscow) 52:651-657). Competition bioassays using a Rhizobium reference strain capable of producing nodules that were visually distinguishable from those produced by normal stains have been used (Eaglesham ARJ et al. (1982) Appl. Environ. Microbiol. 44:611-618). All of these measures are relatively labor-intensive to assess and are not practical for mass screening of isolates or presumptive mutants. Mixed inoculations of a toxin-producing, chlorosis-inducing strain and various normal strains have been used to assess competitiveness (Means UM et al. (1961) Soil Sci. Soc. Proc. 25:105-108). A "blocking" Istrain has also been used to assess competitiveness (Dowling DN et al. (1985) in *Nitrogen Fixation Research Progress*, eds.: Evans HJ et al., p. 141). Those methods are not generally useful, being limited to Rhizobium species having toxin-producing strains or "blocking" strains.

SUMMARY

It is an object of the present invention to contribute to production of rhizobial inoculants. In particular, an object is to contribute to production of inoculants that can out-compete indigenous rhizobia and that can form a larger proportion of root nodules on inoculated legume crop plants than currently available inoculants. In pursuance of this goal, it is an object of the present invention to provide a means for easily screening a collection of strains for those which may have competitive abilities (i.e. Comp variants) above or below a particular criteria. In order to isolate Comp variants (e.g. Comp-) mutants in Rhizobium, a simple, rapid assay is essential. That the assay be generally useful with any species of Rhizobium would also be useful. To date the art has lacked such an assay. It would be possible to isolate such mutants using mixed inocula and nodule typing, but this would prove to be cumbersome and tedious. Using simple mixing assay of the herein disclosed invention, both competition deficient and symbiotic mutants can be screened simultaneously. The symbiotic mutants can then be readily identified using simple tests for biological function and the competition mutants may then be confirmed using simple mixing tests. With this novel screening assay, the art is for the first time provided with a method of general applicability to search for competition variants in Rhizobium species and, as exemplified herein, mutants whose sole known defect is reduced competitiveness.

The present invention is a method for screening Rhizobium cells for competitiveness comprising the step of inoculating a legume plant with a mixture of a test Rhizobium strain and a Rhizobium reference stain, followed by the step of observing the plant's foliage visually for symptoms caused by the reference strain. In particular, the present invention is a method for separating a collection of one or more test Rhizobium strains into a Comp$^{above}$ collection and a Comp$^{below}$ collection by: inoculating a legume plant with a mixture of a Fix+ test Rhizobium strain and a Fix− reference Rhizobium strain, the test and reference strains being both Nod+, and the reference strain not producing a phytotoxin; growing the plant for time sufficient for an uninoculated plant to be yellow due to nitrogen deficiency; and identifying the strain to be Comp$^{above}$ if the plant is green due to nitrogen sufficiency or to be Comp$^{below}$ if the plant is yellow due to nitrogen deficiency, the Comp$^{above}$ and Comp$^{below}$ phenotypes being respectively more or less competitive than a Comp criterion, the criterion being measured relative to the reference strain; whereby the test strain's Comp phenotype relative to the Comp criterion is determined. In other words this method involves competition of Fix+ test strains with a Fix− reference strain followed by observation of whether the foliage is green or yellowish, well known symptoms of nitrogen-sufficiency and nitrogen-deficiency, respectively. Therefore, this screening procedure allows the isolation of competition defective mutants on the basis of plant color. Yellow plants obtained in this assay could result from a mutation in a number of different genes (e.g. nif, nod, fix, or competition genes). When inoculated alone, Fix− and Nod− mutants produce yellow plants, whereas Comp− mutants are defined herein as those that result in a green plant when inoculated alone. Indeed, three mutants defective in nitrogen fixation were also identified during this study. As Fix− mutants can be obtained from any Rhizobium strain that is effective in nitrogen fixation by many means known to the art (e.g transposon mutagenesis), the present invention os of general applicability. Also exemplified herein, Tn5 mutagenesis of Rhizobia has been coupled to this novel bioassay to identify mutants of Rhizobium fredii strain USDA257 that are defective in competition. Tn5and the flanking genomic regions were cloned from two of the mutants, and recombination of these clones into the parent strain showed that Tn5 is responsible for the mutant phenotype. Though the search for Comp− mutants is exemplified herein, the art will recognize that the principles of the herein disclosed bioassay may be used to search for any type of Comp variant. Also, mutagens other than Tn5 may be used.

Competition bioassays using either mixing effective and ineffective strain or visual observations are known to the art (see Background). Despite great interest in interstrain competition, none of the published methods provides a generalized method practical for screening large numbers of strains for strains having competitive ability above or below a particular criteria. Furthermore, although many of these bioassays were disclosed many years ago, the art has not combined them into a simple, generalized competition bioassay suitable for mass screenings. Therefore, it is believed that the herein disclosed bioassay represents a significant advance in the art and fulfills a need for a means for identifying strains of differing competitive abilities from a large collection of strains. It is believed that this bioassay will therefore provide a significantly improved method useful for work attempting to improve agronomically important rhizobial inoculants.

DETAILED DESCRIPTION OF THE INVENTION

The following definitions are provided in order to remove ambiguities to the intent or scope of their usage in the Specification and claims.

Rhizobium: Where the name Rhizobium appears by itself, it refers to both the genus Rhizobium (fast-growers) and the genus Bradyrhizobium (slow-growers); both of these genera were, until recently, classified as "Rhizobium". Where the name Rhizobium appears as part of a binomial, e.g. *Rhizobium fredii* or Rhizobium sp., it refers to the genus Rhizobium and not to Bradyrhizobium. Soybean (Glycine) nodulating strains formerly classified as *Rhizobium japonicum* are now classified as either *Rhizobium fredii* (e.g. USDA191 or USDA257) or *Bradyrhizobium japonicum* (e.g. USDA24 or USDA123).

Test Rhizobium Strain: A Rhizobium strain that is being compared for competitive ability relative to a reference Rhizobium strain. As disclosed herein, test strains are Fix$^+$. Generally a collection of several test strains will be compared to a particular reference strain in a battery of bioassays.

Reference Rhizobium Strain: A Rhizobium strain that is being used as a standard by which to assess the competitiveness of one or more test strains. As disclosed herein, reference strains are Fix$^-$.

Fix$^+$: A phenotype of a Nod$^+$ Rhizobium cell, referring to its ability to fix nitrogen when inoculated on a particular legume plant species or variety.

Fix$^-$: A phenotype of Nod$^+$ Rhizobium cell, referring to its lack of ability to fix nitrogen when inoculated on a particular legume plant species or variety.

Nod$^+$: A phenotype of a Rhizobium cell, referring to its ability to nodulate a particular legume plant species or variety. Nod$^-$ refers to the phenotypic lack of this ability.

Comp: A phenotype of a Rhizobium cell, referring in particular to its ability to compete with other Rhizobium cells in the process of nodulation. The effects of competition between two Rhizobium strains are manifested when the probability that nodule contains a particular strain is not directly proportional to that strain's representation in the inoculum. For example, if equal numbers of strains A and B are inoculated onto a plant but more of the resultant nodules contain A than B, A is said to be more competitive than B. Similarly, if 90% of the cells of an inoculum are strain-P and 10% are strain P does not occupy about 90% of the nodules, strains P and Q are not equally competitive; e.g. if P and Q occupy equal numbers of nodules, P is less competitive than Q. The herein disclosed bioassay measures whether a test strain is above (Comp$^{above}$) or below (Comp$^{below}$), an experimentally set criterion. This criterion is measured relative to a reference strain. Two special Comp$^{above}$ and Comp$^{below}$ phenotypes are used herein: Comp$^+$ (Comp$^{above}$) refers to a wild-type competitive ability and Comp$^-$ (Comp$^{below}$) to decreased ability relative to that wild-type. Differing competitive abilities due to auxotrphy or changed growth properties are not to be considered variant Comp phenotypes.

nif$^-$: A genotype unable to make functional nitrogenase.

Input Ratio: The test strain:reference strain ratio (i.e. the Fix$^+$:Fix$^-$ ratio) as inoculated onto a plant. For example, if an inoculum contains $10^5$ Fix$^+$ cells and $3 \times 10^5$ Fix$^-$ cells, the input ratio is 1:3. Similarly, if an inoculum contains $10^7$ Fix$^+$ cells and $10^6$ Fix$^-$ cells, the input ratio is 10:1. Two bioassays that differ only in input ratios, e.g. 30:1 and 3:1, could be said to differ in input ratios by a certain factor or quotient, in this example ten. Adjustment of the input ratio is used to set the ctiterion.

Transition Ratio: The word "transition" refers to the "transition" of foliage color between green and yellow. When a single strain is being tested, the transition ratio is the input ratio at which an inoculated plant has a one-half probability of being scored as green and a one-half probability of being scored as yellow. For example, if bioassays are preformed at input ratios of 30:1 and 3:1, the former yielding green plants and the latter yielding yellow plants, both bioassays could be said to be within a factor of ten of the transition ratio. A third bioassay at an input ratio of 0.3:1 would be within a factor of one hundred but not within a factor of ten of the transition ratio. In this example, the transition ratio less than 30:1 and greater than 3:1, and might be very roughly estimated to be about 10:1. When a collection of Fix$^+$ mutant strains derived from a wild-type strain, is being screened, the multiple-strain transition ratio is defined as the single-strain transition ratio of the wild-type strain. These mutant strains can differ from the wild-type by being chemically-induced point mutants or by having inserted DNA (e.g. a transposon or a plasmid). When a collection of Fix$^+$ natural isolates is being screened, the multiple-strain transition ratio is defined as the mean of the single-strain transition ratios.

Criterion: A measure of competitiveness. Strains more competitive than the criterion of a particular bioassay are scored as Comp$^{above}$ while those less competitive than the criterion are scored as Comp$^{below}$. The criterion is set by adjusting the input ratio. The criterion can serve as a quantitative measure of how competitive a strain is. For instance, if the input ratio of a bioassay is 1000:1, one might say that a test strain scored as Comp$^{above}$ (i.e. plants are green) is at least about a thousand-fold more competitive than the reference strain. Similarly, if the same experiment the test strain is scored as Comp$^{below}$ (i.e. plants are yellow), one might say that it is less than about a thousand-fold more competitve. (Indeed it might be less competitive than the reference strain.) A criterion is set relative to a reference strain. For example, if X and Y are two Fix$^-$ reference strains used in different experiments to measure the Comp phenotype of Fix$^+$ test strain Z, and if X is ten-fold more competitive than Y (i.e. when an inoculant having about 100 Y cells for every X cell gives a nodule occupancy of about 90% Y and about 10% X), then a Z:X input ratio of 100:1 and a Z:Y input ratio of 1000:1 are at about the same criterion and Z will be scored (e.g. Comp$^{above}$ if green plants are observed) identically in both the Z:X and the Z:Y bioassays.

Substrate: The material the seed is cultured in during a bioassay. Artificial materials include vermiculite, perlite, paper, agar, parafin, and the like, while natural materials include soil and sand.

Natural Isolate: A Rhizobium strain essentially unaltered from a cell isolated from soil or root nodules. For the purposes of the present invention, derivatives of natural isolates are considered functionally equivalent to natural isolates if they are essentially unaltered except for the presence of a drug resistance marker or another genetic marker that is useful for strain identification and does not affect any of the symbiotic nitrogen metabolism properties.

Inserted DNA: The DNA sequences in a cell which were not present in the natural isolate ancestor of that cell. Inserted DNA can include transposons, recombinant DNA plasmids, DNA segments from other Rhizobium strains, and the like.

Phytotoxin: A chemical capable of causing a plant not to appear healthy, e.g. to be yellow.

Nitrogen Deficiency: Lack of enough fixed nitrogen to properly support plant growth. It is well known to the art that when a plant does not have sufficient nitrogen, it will display certain symptoms, including having foliage that is yellowish or yellow rather than green. The appearance of nitrogen-deficient and nitrogen-sufficient plants may be easily seen without undue experimentation by means well known to the art.

I have invented a means for visually screening a collection of Rhizobium strains, thereby identifying strains likely to have changed Rhizobum-Rhizobium competition properties. The fundamental aspect of this method is competition of a Fix+ strain thought to be changed in competitive properties with a Fix− strain. When searching for Fix+ strains having decreased competitiveness, one chooses an input inoculum ratio (Fix+:Fix−) such that Fix+ cells form enough nodules to supply the inoculated plant with nitrogen, i.e. so that the plant is green. However, the input ratio is set low enough that, if the Fix+ strain has reduced competitiveness, not enough nodules will be formed by the Fix+ cells to provide adequate nitrogen to the plant. The plant will therefore display symptoms of nitrogen deficiency; in particular, the plant will appear yellowish. Conversely, when searching for Fix+ strain having increased competitiveness, one chooses an input ratio such that Fix+ cells do not form enough nodules to supply the plant with sufficient nitrogen. At this input ratio the plant is yellow. However, the input ratio must be high enough that if the Fix+ has increased competitiveness, the Fix+ cells can out-compete the Fix− cells, thereby forming more nodules. The increased number of Fix+ bacteroids must be sufficient to provide the inoculated plant with sufficient fixed nitrogen, thereby causing the plant to appear green.

Many conditions and materials used in this competition bioassay may be varied. Examples include, but are not limited to, substrate (e.g. soil or vermiculite), Fix− bacterial strain, Fix+ bacterial strains, legume species or cultivar, type of mutagen, plant and bacterial growth conditions, plant age at the time of inoculation method of inoculation, method of measuring bacterial input ratios, time between inoculation and scoring, and the like. The art will recognize that variation of any one of these conditions or materials may result in the need to make adjustments or changes in other conditions or material. However, these adjustments or changes may be made without undue experimentation and are well understood by those of ordinary skill in the art of competition bioassays. It is understood that any particular embodiment of the bioassay disclosed herein, though capable of detecting many Comp loci, may not reveal all possible Comp mutants. For example, genes which affect competition on a particular plant cultivar or in a particular bioassay substrate (e.g. a particular type of soil) may not affect competition on the cultivar or in the substrate used in the bioassay. However, changing conditions to a different cultivar or genotype may then permit detection of genetic loci not detected under the original conditions, as is understood in the art. It will be understood in the art that any particular Comp mutant may compete differently when conditions are changed, e.g. changing the test substrate from vermiculite to soil, or competing in a field rather than a laboratory screening. However, the exact behavior of any particular allele of any particular Comp gene may be determined by those of ordinary skill in the art without undue experimentation using techniques well known to the art, in addition to the herein disclosed visual competition bioassay technique.

The type of mutagen used can be varied and may affect the types of Comp mutants detected. Chemical mutagens, use of which is well known to the art of bacterial genetics, may possibly generate missense mutations in essential non-Comp genes that affect an essential function without eliminating that function. The effect on the essential function may lower the competitiveness relative to the wild-type parent of a strain carrying that mutation. Transposon mutagenesis, e.g. as exemplified herein with Tn5, can also lead to misleading results. An insertion into the 3'-end of an essential gene's coding sequence might lower competitiveness without eliminating the essential function, as described above for missense mutations. The art will recognize that transposon mutagenesis can lead to polar effects. In other words, when a transposon inserts into a gene of a multi-gene operon, genes downstream from the interrupted gene may be expressed at reduced levels. If one of these downstream genes is a nod, nif, or essential gene, competitiveness may be decreased or yellow plants may result from inoculation with that mutant.

Any Fix− strain may be used as long as that strain is significantly competitive. (Though any Fix− strain may be used, for the convenience of those in the art, EA213, which is used in the Examples, has been deposited as NRRL B-18031 with the Northern Regional Research Center, USDA, 1815 N. University Ave., Peoria, Ill. 61604 USA.) It is advantageous that the mutation be well-defined. An example of a reliable genetic lesion is a deficiency in nitrogenase, which is exemplified herein by the nifD− B. fredii strain EA213. The lesion should also affect a late step in nodulation, not an early step, again so that the Fix+ strain will not complement the Fix− strain. One must also be sure that the Fix− lesion is not really a delayed nodulation or reduced nodulation phenotype and that normal nodules are produced. It is also preferable the the Fix− lesion not be due to lack of production of a diffusable factor as in the bioassay the Fix+ strain may provide the factor to the Fix− strain. The lesion should not affect survival of the Fix− strain in the bioassay substrate (vermiculite as exemplified herein) or in nodules. The suitability of a Fix− strain can be established in a competition bioassay of the Fix− strain with its Fix+ parent under the conditions that will be used to screen presumptive Comp− mutants.

The ratios of the Fix+ and Fix− strains are crucial. If the Fix+:Fix− ratio is too low, all of the plants will be yellow, while if that ratio is too high, all plants will be green. Input Fix+:Fix− ratios of a control bioassay between a Fix− strain and an unmutagenized, presumably Comp+, parent strain must be adjusted to so that plants having a high ratio are green and plants having a low ratio are yellow (e.g. see Table 1, USDA25-7:EA213). It is advantageous to use several different input ratios for each strain being screened. This provides a control to help assure that the assay is being performed near the transition ratio, i.e. near the transition between nitrogen-sufficiency and nitrogen-deficiency. This also provides a means for preliminary assessment of relative competitive efficiencies of Rhizobium strains identified by the herein disclosed bioassay.

One must take care in measuring cell numbers of the Fix+ and Fix− strains used to calculate an input ratio. As exemplified herein, cells were usually grown and then titered, storing the cultures in the cold while the cells being titered were growing. After the culture titers were known, cells were mixed appropriate ratios of cells from the stored cultures for use in the bioassay. Tests showed that cell number does not change significantly while in cold storage for the period of time needed to titrate cultures. Alternatively, one may estimate culture titer, perhaps using a spectrophotomer to measure optical density (O.D.) or directly counting cells visualized in a microscope, and then immediately mix the cells and inoculate them in the bioassay. The exact titers and ratios can then be determined while the bioassay is being performed. The absolute number of cells added may be varied as long as it is high enough that good nodulation is assured.

The quotient of, or ratio between, the input inoculation ratios is important but not crucial. This quotient is exemplified in Table 1 where plants were inoculated at 10:1, 1:1, 1:10, a ten-fold difference between most similar inoculation ratios and a hundred-fold difference between the least similar. For example, I found that a thirty-fold quotient (e.g. 30:1, 1:1, 1:30) was capable of detecting Comp− mutants as well as the ten-fold quotient. Increasing the quotient will decrease the chances of finding mutations while increasing the chance that any particular mutant will contribute strongly to competition under the particular bioassay conditions. Those skilled in the art will recognize that adjusting the ratio may prove useful, depending on whether or not one wishes to detect genes having marginal effects on competition.

One may set the criterion for competitiveness of the identified strains by adjusting the quotient of, or ratio between, the input ratio and the transition ratio, as will be well understood by those in the art. For instance, screening at an input ratio a thousand-fold below the transition ratio will tend to detect variants more competition-deficient than when screening a hundred-fold below the multiple-strain transition ratio. Similarly, screening at an input ratio a thousand-fold above the mutiple-strain transition ratio will tend to detect variants that are more competitive than those detected when screening a hundred-fold above the transition ratio.

It is also important that the physiological state of the two competing cultures be as identical as possible. For example, the competitiveness of a late log phase culture may be different than that of a stationary phase culture of the same strain. In the preferred embodiments, inocula are prepared from stationary phase cultures. However, the particular physiological state may be varied as freshly prepared cultures and cultures stored for five days at 4° C. have been used in the bioassay with similar results. Those in the art will recognize that the cells in any particular culture can have a mixture of physiological states and need not be exactly identical.

It is possible to vary the bioassay substrate. For example, though in the preferred embodiments, the competition bioassay is performed in vermiculite, the bioassay may also be performed in a low-nitrogen soil. It is essential that the soil have very little fixed nitrogen, otherwise the plants will all grow without symbiotic nitrogen fixation and will all be green. Use of low nitrogen soil rather than a nitrogen-free substrate may increase the amount of time between start of the bioassay and when results may be scored. All plants will be green for one to two weeks after the bioassay is started as seedlings use up the nitrogen stored in their cotyledons. The presence of a little fixed nitrogen in the substrate (e.g. in a low nitrogen soil) will further extend the time before the plants begin to turn yellow. After plants begin to turn yellow, one should wait a week or two before scoring plants as yellow or green to assure unambiguous results. Searches for Comp mutants in many Rhizobium species, e.g. alfalfa-nodulating *R. meliloti* or clover-nodulating *R. trifolii,* might be usefully done on an agar medium contained by test tubes rather than in vermiculite contained by Leonard jars. Indeed, B. japonicum and *R. fredii* strains can be screened similarly using the wild soybean, *Glycine soja,* which has very small seeds. Experiments under laboratory conditions, e.g. in vermiculite will often, but not always, be predictive of behavior under field conditions.

The age of test plants at the time of inoculat-ion may be varied provided that the plants are still competent for nodulation. Timing of competency for nodulation is well known to the art and is simply determined, without undue experimentation, by doing a time-course of nodules produced vs. age of plant at time of inoculation. It will be understood to those in the art that different Comp loci may affect competition differently on plants of different ages or roots of different ages, that not all Comp loci may be detectable with plants of a particular age, and that varying the time of inoculation may be useful for detecting different loci.

The art will recognize that it is crucial when performing the bioassay disclosed herein that there be no cross-contamination of inocula between test plants. Such cross-contamination can change both input ratios and input Fix+ genotypes, thereby rendering false data. Therefore, it is essential that before performing the disclosed bioassays, one must establish that, under the particular bioassay conditions, there is no cross-contamination between plants in separate containers (e.g. Leonard jars). Such testing is well understood in the art and may be simply done by doing a series of bioassays where some plants are not inoculated. Presence of root nodules on uninoculated plants indicates cross-contamination. Those in the art will recognize that it is also important that strains and inocula not be contaminated before the inoculation step. Such contamination may be checked by a number of methods known to the art.

The herein disclosed visual competition bioassay will also detect mutants of genes other than Comp genes. By definition, a Comp− phenotype should not be due to auxotrophy or changed growth properties, e.g. a change in growth rate or the start of growth when coming out of stationary phase. The former may be tested by growth on minimal media while the latter may be tested by placing inocula in various growth media and, during growth, seeing if ratios between the component strains change. Nod− and Fix− mutants will also yield yellow plants. These lesions can be detected in a modified bioassay by inoculating with only the presumptive Comp− strain, i.e. by inoculating without mixing the presumptive Comp− strain with a known Fix− strain. Under this condition, Comp− strains will generate green plants and Fix− or Nod− strains will generate yellow plants.

Any presumptive Comp mutations must be confirmed by nonvisual competition bioassays. Several, optimally at least five, replicates of the experiment should be done and quantitative data on nodule occupancy should be obtained. Quantitation of competition between Rhizobium strains is well known to the art. Nodule occupancy also requires many replicates; optimally at least sixteen nodules per plant should be typed. Strains may be identified by means known to the art, including presence of characteristic plasmids or DNA restriction fragments or, as exemplified herein, antibiotic-resistance markers. Identity of strains may also be confirmed by serotyping. Strain identification is also useful for detecting any contaminants in a particular test. Multiple repetitions of experiments decreases the probability of false negatives or false positives due to errors in scoring.

As examplified herein, the bioassay is used to detect mutants having Comp⁻ phenotypes. Such phenotypes may also be thought of as Comp$^{decreased}$ rather than as Comp$^{defective}$. The Comp⁻ mutants are detected by identification of yellow plants at inoculation input ratios that with the parent Rhizobium strain normally give green plants. The bioassay may easily be modified to detect a Comp$^{increased}$ phenotype. Presumptive Comp$^{increased}$ mutants can be produced by methods well known to the art of recombinant DNA manipulations including, but not limited to, introduction of random DNA fragments from a first relatively highly-competitive strain into a second less-competitive strain following by visual screening for increased competitiveness, relative to the second strain itself, of the derivatives of the second strain.

EXAMPLES

The following Examples are presented for the purpose of illustrating specific embodiments within the scope of the present invention without limiting the scope, the scope being defined by the claims. Numerous variations will be readily apparent to those of ordinary skill in the art.

These Examples utilize many techniques well known and accessible to those skilled in the arts of molecular biology; such methods are fully described in one or more of the cited references if not described in detail herein. Enzymes are obtained from commercial sources and are used according to the vendor's recommendations or other variations known to the art. Reagents, buffers, and culture conditions are also known to those in the art. Reference works containing such standard techniques include: Wu R, ed. (1979) Meth. Enzymol. 68: Wu R et al., eds. (1983) Meth. Enzymol. 100 and 101; Grossman L and Moldave K, eds. (1980) Meth. Enzymol. 65; Miller JH (1972) *Experiments in Mulecular Genics*: Davis R et al. (1980) *Advanced Bacterial Genetics*; Schleif RF and Wensick PC (1982) *Practical Methods in Molecular Biology*; Maniatis T et al. (1982) *Molecular Cloning*; and Rodriguez RL and Tait RC (1983) Genet. Engin. 4:1–56.

Textual use of a restriction endonuclease name in isolation, e.g. "EcoRI", refers to use of that enzyme in an enzymatic digestion. Restriction sites are indicated by the additional use of the word "site", e.g. "EcoRI site". The additional use of the word "fragment", e.g. "EcoRI fragment", indicates a linear double-stranded DNA molecule having ends generated by action of the named enzyme (i.e. a restriction fragment).

Strains parenthetically indicate a plasmid harbored within, e.g. *E. coli* MM294 (RP4-4::Tn7). All exemplified recombinant DNA constructions can be done using starting materials well known and widely available to the art or which are harbored by deposited strains.

EXAMPLE 1

Genetic Materials

The strains used were as follows: 257spc-2 is a mutant of USDA257 (Keyser HH et al. (1982) Science 215:1631–1632) resistant to 0.25 mg/ml spectinomycin; TML90, TML54, TML41 and TML125 are Tn5 induced mutants of 257spc-2 defective in competition; TML89 is a Tn5 containing 257spc-2-derivative unaffected in competition, nodulation, or nitrogen fixation; TML90-11 and TML54-15 are recombinants in which double homologous recombination has substituted the Tn5 containing region from mutant TML90 and TML54, respectively, for the corresponding wild-type fragments of 257spc-2; and *R. fredii* EA213 (NRRL B-18031) (Appelbaum E et al. (1985) in *Nitrogen Fixation Research Progress*, eds: Evans HJ et al., ISBN 90-247-3255-7, pp.101–107) is a Fix⁻ mutant of 191str having Tn5 in its nifD gene. Soybean seeds (*Glycine max* cv. Peking) were obtained from D. Bernard, USDA, Urbana, Ill.

EXAMPLE 2

Transposon Mutagenesis

The transposon Tn5was introduced into *R. fredii* strain USDA257spc using SM10(pSUP1011) as described by Simon R et al. (1983) Biotechnol. 1:784–791. The donor and recipient strains were mixed together at a 5:1 ratio before being transferred onto TYA plates (Beringer J (1973) J. Gen. Microbiol. 84:188–198) and incubated at 30° C. for 2 days. The bacteria were then harvested in PBS (phosphate buffered saline: 0.523 g $K_2HPO_4$, 0.408 g $KH_2PO_4$, 7.09 g NaCl, $H_2O$ to 1.0 l) and diluted and plated onto selective plates containing antibiotics and tested for their competitive ability in competition with EA213.

EXAMPLE 3

Leonard Jars

Leonard jars (Leonard LT (1944) U.S.D.A. Circ. No. (703; see also Vincent JM (1970) *A Manual for the Practical Study of the Root-Nodule Bacteria*, IBP Handbook No. 15, Blackwell Scientific Publications, Ltd., Oxford, pp. 86–90) were not made of glass. Instead the upper and lower chambers were both plastic Magenta boxes, commonly used in the art of plant tissue culture. The upper chamber had a hole drilled in the bottom through which ran a wick made of rope. These modified jars are very convenient for mass screenings of inoculated plants, being made of unbreakable, autoclavable materials. Having square bases they were easily manipulated and placed in densely packed arrays.

EXAMPLE 4

Competition Bioassay of *R. fredii*

Competition studies were carried out in Leonard jar assemblys containing vermiculite and a nitrogen-free nutrient solution. Seeds were surface sterilized in undiluted commercial bleach for about 10 min., followed by 6 rinses with sterile distilled water, followed by soaking in 0.036N HCl for about 5 min., followed by another 6 rinses. Seeds were placed in sterile vermiculite and about 1 ml of inocula containing about $0.5-1.0\times10^9$ cell/ml were poured over the seed. Seeds were then germinated in sterile vermiculite in the dark for 2 or 3 days. A layer of parafin-coated sand was then placed over the vermiculite and the seeds were placed in a light:dark regime suitable for growth of the soybean cultivar. Cultures of the strains to be tested were grown to saturation in TY broth (Boeringer J (1979) J. Gen. Microbiol. 84:188–198). Total viable cell counts were carried out on TYA (TY broth solidified with 1.5% agar) and the cells held at 4° C. until results were obtained. In separate experiments, it was determined that storage had no effect on viable cell numbers and did not affect the competitive properties of these strains. Inoculation was carried out by mixing the strains at the indicated ratios in sterile distilled water and applying the suspension immediately to the plants, to give approximately $1 \times 10^8$ cells per pot. Each treatment was replicated five times. The plants were grown in a growth chamber for 35 days at 22° C.:20° C. (day:night) temperature and watered as required with a nitrogen-free solution (Cutting JA and Schulman HM (1969) Biochim. Biophys. Acta 192:486–493). Plant color was scored visually after approximately 4 weeks of growth. Yellow plants resulted when EA213 formed the majority of the nodules because EA213 cells cannot fix nitrogen. Yellow plants also arose when the 257spc-2 derivative was itself phenotypically defective in nodulation (Nod$^-$), nitrogen fixation (Fix$^-$), or competition (Comp$^-$). Sixteen nodules were selected per plant, making a total of 80 per treatment. Nodules were sterilized by washing in 0.5% sodium hypochlorite for about 15 min. and in 3% hydrogen peroxide for about 10 min. before washing in 6 changes of sterile distilled water. Nodule occupancy was determined after crushing the nodules in sterile PBS, and transferring to TYA agar with the appropriate antibiotics. EA213 is sensitive to spectinomycin and resistant to high levels of streptomycin (1.0 mg/ml). The 257spc-2 derivatives are resistant to spectinomycin and sensitive to high levels of streptomycin.

EXAMPLE 5

Bioassay Results

The fast-growing *R. fredii* strains USDA257 and USDA191 are Fix$^+$ on the *Glycine max* cultivar Peking (Keyser HH et al. (1982) Science 215:1631–1632). In vermiculite a spectinomycin-resistant derivative of strain USDA257 and EA213 are of equal competitiveness (Table 1). When inoculated at a 1:1 ratio about half of the nodules are formed by each strain and the plants are green. At a 10:1 ratio in favor of EA213, approximately 90% of the nodules are formed by EA213, and the resulting plants are yellow due to nitrogen deficiency. This visual color assessment is the basis of the assay used to isolate competition deficient mutants. USDA257spc-2 was mutagenized using Tn5, a 5.8 kbp (kilobase pair) transposon (Berg DE and Berg CM (1983) Biotechnol. 1:417–435), conferring kanamycin resistance which was introduced by the SM10 (pSUP1011) suicide plasmid delivery system (Simon R et al. (1983) BioTechnol. 1:784–791). Six hundred randomly chosen kanamycin resistant transconjugants were individually coinoculated with EA213 on G. max cv. Peking plants at a 10:1 ratio in favor of the 257spc-2 derivative. If the Tn5-harboring strain was competitive with EA213, it formed the majority of the nodules and a green plant resulted. If a phenotypically competition deficient (Comp$^-$) mutant resulted from Tn5 insertion, EA213 formed the majority of the nodules and the plant appeared yellow. Plants inoculated with phenotypically Nod$^-$ and Fix$^-$ strains also would appear yellow.

Seven transconjugants were isolated that gave yellow plants in competition with EA213. Serotyping and analysis of plasmid content confirmed that these transconjugants were derivatives of 257spc-2. Three strains were symbiotically defective when inoculated alone, i.e. they were Fix$^-$. Even when coinoculated with EA213 at a 10:1 ratio in their favor, the remaining four mutants (TML90, TML41, TML125, and TML54) produced yellow plants and occupied a significantly lower percentage of nodules than the wild type strain 257spc-2 (Table 1). These four mutants, which no longer harbored the pSUP1011 suicide plasmid, were also competition deficient in a field experiment when tested against a high indigenous population (Table 2). The field experiment was carried out in a Ringwood silt loam, near Sun Prairie, Wis. The most probable number (MPN) of indigenous rhizobia (Brockwell J (1963) Appl. Microbiol. 11:373–383) was $3.5 \times 10^5$ cells/gm of soil. The study consisted of seven treatments each replicated four times using a randomized complete block layout. The treatments were: USDA257spc-2, the mutants TML89 (contains a Tn5 insertion), TML90, TML54, TML41, TML125, and an uninoculated control. Plots (1.25 m × 3 m) were planted with a two row planter at a rate of 1 seed/2.5 cm row with soybean cv. Peking in 1.25 m long rows spaced 1 m apart. Liquid inocula (400 ml undiluted cells in TY) were added over the seeds postplanting with a sprinkling can. Total viable cell counts were carried out on TYA with the appropriate antibiotics. The number of cells added per seed is indicated in Table 2. Eight plants per replication were selected for analysis 40 days after planting. Four nodules were harvested from each plant, making a total of 128 per treatment. Nodule occupants were identified using antibiotic resistances; nodule surface sterilization was described by McLoughlin TJ et al. (1985) Can. J. Microbiol. 31:220–233. Variance analysis of the data subjected to arcsin transformation (Snedecor GW and Cochran WG (1973) *Statistical Methods*. 6th Ed., Iowa State Univ. Press, Ames, Iowa) showed significant (P=0.05) differences between the strains in competing for nodule sites with the indigenous Rhizobium population. The four mutants were also competition deficient when tested in Leonard jars in a growth chamber against the parent USDA257spc-2.

When inoculated alone, no significant differences were detected between these four mutants (TML90, TML41, TML125, and TML54) and the wild-type (USDA257) in nodule mass, nodule numbers, acetylene reduction activity (Hardy RWF et al. (1968) Plant Physiol. 43:1185–1205), or plant dry weight after 35 days of growth. Other characteristics, including motility, growth on minimal medium, and days to first nodule formation, were also measured. No significant differences were detected between the mutants and the wild-type except in the case of TML125, which was delayed in nodulation. Competitiveness for growth on the legume root surface (i.e. the rhizosphere), measured as described by Brewin NJ et al. (1983) J. Gen. Microbiol. 129:2973–2977, was not significantly different between TML90 and TML89 when mixed with EA213 at 1:1, 10:1, and 1:10 input ratios. Thus, three mutants (TML90, TML41, and TML54) specifically defective in competition for nodulation on soybean roots were isolated.

EXAMPLE 6

DNA Analysis

DNA was prepared from the competition defective mutants by the method of Scott KF et al. (1981) J. Mol. Appl. Genet. 1:906-911. Approximately 0.001 mg of DNA was digested with EcoRI (Bethesda Research Laboratories), separated by agarose gel electrophoresis and transferred to nitrocellulose (Southern EM (1975) J. Mol. Biol. 98:503-517). Hybridization with pKS4 (Murai N et al. (1983) Science 222:476-482) was done as described by Appelbaum EA et al. (1982) Science 215:1631-1632. pKS4 can be isolated from E. coli C600 (pKS4) which has been deposited as NRRL B-15394. pKS4 is a pBR322 subclone of Tn5-derived BamHI/-HindIII fragment of pRZ102 (Jorgensen RA et al. (1979) Mol. Gen. Genet. 177:65-72) encoding a kanamycin resistance gene. Southern blot analysis of EcoRI digested genomic DNA of the mutants using the Tn5-specific probe revealed that TML90 and TML54 each have a single Tn5 insertion, respectively resulting in fragments of about 15 kbp (kilobase pairs) and about 10 bp while TML41 showed two hybridizing fragments (about 10 kbp and about 6.0 kbp). The mutants are different based on the size of the restriction fragments into which Tn5 is inserted.

Plasmid DNA was isolated using the modified Eckhardt procedure described by Simon R (1984) Mol. Gen. Genet. 196:413-420. Transfer of plasmid DNA to nitrocellulose filters and hybridization conditions were the same as described above. Tn5 was found to be in a chromosomal location in TML90 and TML54 while TML41 had two insertions in the chromosome and one in the symbiosis plasmid.

EXAMPLE 7

Cloning of Comp⁻ Mutant DNA

Total genomic DNAs from TML90 and TML54 were prepared using the method of Scott KF et al., supra. The DNA was digested with EcoRI, ligated into the EcoRI site of the tetracycline-resistant vector pSUP202 (Simon R et al. (1983) Biotechnol. 1:784-791) and transformed into E. coli MC1061 (Shapira SK et al. (1983) Gene 25:71-82). Selection was made for colonies resistant to both kanamycin (0.025 mg/ml) and tetracycline (0.010 mg/ml) on LB (Miller JH (1972) *Experiments in Molecular Genetics* (Cold Spring Harbor Laboratory, Cold Spring Harbor, N.Y.)) at 37° C. Plasmid DNA was isolated using the technique of Klein RD et al. (1980) Plasmid 3:88-91, and transformed into E. coli S17-1 (deposited as NRRL B-15483; Simon et al., supra) with selection for colonies resistant to kanamycin and tetracycline. Analysis of the resulting clones revealed that TML41 actually had three copies of Tn5, two of them residing in fragments of nearly identical size but with different restriction maps. Clone pS90 had an insert of about 15 kbp while pS54 had an insert of about 10.3 kbp.

In order to prove that Tn5 was responsible for the mutant phenotype, pS90 and pS54 were transferred back into 257spc-2 from S17-1, with selection for transconjugants that were resistant to spectinomycin and kanamycin on minimal medium (Bishop PE et al. (1976) Plant Physiol. 57:542-546). To identify transconjugants in which Tn5 had recombined back into the 257spc-2 genome as the result of a double homologous recombination event, tetracycline sensitive transconjugants were identified. Total genomic DNA was isolated from these strains and subjected to hybridization analysis (Southern EM, supra). DNA was prepared, digested with EcoRI, and hybridized with $^{32}$P-labeled pS90 DNA as described above. 257spc-2 had a single approximately 15 kbp band. Mutant TML90 and transconjugant 90-11 had identical single bands at about 15 kbp, indicating that a double homologous recombination event had occurred in TML90-11. DNA was also prepared, digested with EcoRI, and hybridized with $^{32}$P-labeled pS54 DNA. 257spc-2 had a single approximately 4.8 kbp band. Mutant TML54 transconjugant TML54-15 had identical single bands at about 10 kbp, indicating that a double homologous recombination event had occurred in TML54-15. As Tn5 is about 5.8 kbp in size, the wild-type EcoRI fragments corresponding to the Tn5 insertions of TML54 and TML90 were calculated to have approximate sizes of about 4 kbp and about 9 kbp, respectively. The majority of the tetracycline sensitive transconjugants had suffered transposition of Tn5 to another location in the genome. However, from each mating, a single recombinant with the desired genotype was obtained (TML54-15 and TML90-11). As shown in Table 1, these recombinants containing Tn5 in the desired location were also competition defective, thus proving that Tn5 is responsible for the mutant phenotype in TML54 and TML90.

EXAMPLE 8

Cosmid Cloning of Como+ Wild-Type DNA pSym DNA was isolated from wild-type R. fredii USDA257 by the method of Scott, supra. This DNA was partially digested with EcoRI and the resulting fragments were fractionated by centrifugation through a salt gradient. Fractions were screened by agarose gel electrophoresis and those which contained significant quantities of 40 kbp DNA fragments were pooled. The about 40 kbp DNA was mixed with and ligated to EcoRI-linearized pSUP205 DNA (Simon R et al., supra). Long USDA257 DNA/pSUP205 DNA concatamers were packaged into bacteriophage lambda particles using a commercially available phage lambda packaging system (Packagene (R): Promega Biotec., 2800 S. Fish Hatchery Rd., Madison, Wis. 53711, USA; lambda packaging is a technique well known in the art). E. coli K802 cells were then infected with the resulting cosmid-containing virions and selected for resistance to tetracycline. Resistant colonies were screened for loss of chloramphenicol-resistance and subjected to colony hybridization procedures well known in the art. Colony blots were hybridized individually with two different probes, an about 15 kbp pS90 probe and an about 10 kbp pS54 probe. These probes were prepared by digestion of the appropriate plasmid with EcoRI, agarose gel electrophoresis of the resulting mixture of restriction fragments, electroelution of the fragment having the appropriate size, and nick translation of the resulting isolated fragments. Plasmid DNAs were isolated from two tetracycline-resistant, chloramphenicol-sensitive, hybridization-positive colonies by a small-scale, alkaline-lysis, plasmid-isolation procedure (miniprep) well known to the art which hybridized to pS54 and from two similar colonies which hybridized to pS90. These plasmid DNAs were analyzed by digestion with EcoRI followed by gel electrophoresis of the resulting fragments. The clones that hybridized with pS54 both contained a number of common fragments including one expected fragment of about 4 kbp. Similarly, the clones that hybridized with pS90 both contained a number of common fragments including one expected fragment of about 9 kbp. The plasmids which hybridized to pS54 had no fragments in common with those which hybridized to pS90. Two cosmids were chosen for further work: 954, which hybridized to pS54, and 390, which hybridized to pS90. The inserts of the other two cosmids were found not to be stable, as the art knows to be true for many cosmids.

RP4-4 is a mobilizing helper plasmid which is a neomycin-sensitive derivative of RP4 (Hedges RW and Jacob AE (1974) Mol. Gen. Genet. 132:31-40; see also Simon R et al. (1983) in *Molecular Genetics of Bacteria-Plant Interactions*, ed.: Pühler A, pp. 98-106). RP4-4::Tn7, a derivative of RP4-4 having its tetracylcine-resistance gene inactivated by insertion of Tn7, was harbored by *E coli* MM294 (see Ruvkin GB and Ausubel FM (1981) Nature 289:85-88; also Davis et al., supra). Cultures of *E. coli* MM294 (RP4-4::Tn7) and *E. coli* K802 rec- (cosmid), the cosmid being either 954 or 390, were mated by being first mixed together, incubated overnight on a nitrocellulose filter, resuspended, and then selected for the cosmid-borne tetracycline-resistance and a Tn7-borne spectinomycin resistance. The selected colonies were further tested for an RP4-borne ampicillin resistance. RP4-4::Tn7::cosmid cointegrates did not form in the rec- host.

Resultant *E. coli* K802 rec- (cosmid) (RP4-4::Tn7) cells were then mated, as described above, with a *Rhizobium fredii* mutant, thereby introducing cosmids 954 and 390, into TML54 and TML90, respectively. Selection for tetracycline-resistance resulted in identification of colonies, designated 954Rj1 and 390Rj1, having the its introduced cosmid integrated by a single homologous recombination event into the *R. fredii* chromosome. RP4-4::Tn7 was not present in these cells, being lost due to lack of selection for spectinomycin resistance. 954Rj1 and 390Rj1, and wild-type USDA257 were competed against EA213 in the competition bioassay. Introduction of the wild-type sequences of 954 and 390 into TML54 and TML90, respectively, are observed to result in cells that are approximately equivalent to wild-type USDA257 in competitiveness.

*E. coli* K802 rec- (RP4-4::Tn7) (cosmid) cells, where the cosmid was either 954 or 390, were mated with *Rhizobium meliloti* 1021 str$^r$ cells. Selection for resistance to both streptomycin and tetracycline resulted in identification of cells harboring cointegrates of the cosmid and the mobilizing plasmids. These *R. meliloti* 1021 str$^r$ (RP4-4::Tn7::954) cells and 1021 str$^r$ (RP4-4::Tn7::390) were then mated with TML54 and TML90, respectively. After selection with 0.25 mg/ml spectinomycin and 0.01 mg/ml tetracycline, colonies, designated 954Rj2 and 390Rj2, were identified which harbored RP4-4::Tn7::cosmid as an independent replicon; i.e. 954 and 390 were not respectively integrated into the TML54 and TML90 chromosomes. 954Rj2, 390Rj2, and USDA257 were competed against EA213 in the competition bioassay. Introduction of the wild-type sequences of 390 into TML90 was observed to restore competitiveness approximately to the level observed for wild-type USDA257. Similar results are observed for introduction of 954 sequences into TML54.

*R. meliloti* 1021 str$^r$ cells grow in dry, nonshiny colonies, while *R. fredii* USDA191 and *R. fredii* EA213 cells grow in gummy, shiny colonies. *R. meliloti* 1021 str$^r$ (RP4-4::Tn7::954) and 1021 str$^r$ (RP4-4::Tn7::390) were both mated with both USDA191 and EA213. Selection for shiny, tetracycline-resistant colonies identified *R. fredii* transcongugants. Presence of the RP4-4::Tn7::cosmid plasmids and identity of the *R. fredii* host were confirmed by gel electrophoresis (Eckhardt T (1978) Plasmid 1:584-588) and serotyping. USDA191 (RP4-4::Tn7::954), USDA191 (RP4-4::Tn7::390), EA213 (RP4-4::Tn7::954), EA213 (RP4-4::Tn7::390), and USDA257 are then competed against EA213 in the competition bioassay. When tested in vermiculite, EA213, USDA191, and USDA257 are about equal in competitiveness, while in soil USDA257 is more competitive than USDA191 or EA213.

EXAMPLE 9

Competition Bioassay of *B. japonicum*

A Comp- mutant of the *Bradyrhizobium japonicum* strain USDA123 spc$^r$ was also isolated. Tn5 was introduced into USDA123 spc$^r$. About 1300 kanamycin-resistant USDA123 spc$^r$::Tn5 transconjugants were competed against the Fix- *B. japonicum* strain USDA24 (USDA24 is well known to the art and is available from the Rhizobium Culture Collection, U.S. Department of Agriculture, Beltsville, Md.). Ten Sym mutants were identified. These ten mutants included strains having phenotypes of Nod$^{delayed}$, Fix-, and Comp-; one Comp- mutant was identified. It produced green soybean plants when inoculated alone; i.e. it was shown not to be Fix- or Nod-. It was confirmed to be Comp- by nodule typing.

EXAMPLE 10

Interpretation of Results

The DNA analysis and cloning experiments (Examples 6, 7, and 8) indicated that the Tn5 insertions were responsible for the Comp- phenotypes of the *R. fredii* variants made in Example 2 and identified in Examples 4 and 5. These experiments further showed the herein disclosed visual bioassay to be useful for identifying Comp variants. The identification of the *B. japonicum* Comp- mutant (Example 9) extended these conclusions by demonstrating the present invention to be useful for identification of Comp variants of strains of both the genus Rhizobium and the genus Bradyrhizobium.

TABLE 1

| Competition Studies With Comp- Mutants and Transconjugants | | | | | | |
|---|---|---|---|---|---|---|
| Strains Fix+:Fix- | Input Ratio Fix+:Fix- | Plant Color | % Nodules Formed by | | | Significance$^a$ |
| | | | Fix+ | Fix- | Both | |
| USDA257:EA213 | 1:10 | Yellow | 14 | 86 | 0 | NS |
| | 1:1 | Green | 54 | 45 | 2 | NS |
| | 10:1 | Green | 93 | 7 | 0 | NS |
| TML90:EA213 | 1:10 | Yellow | 0 | 100 | 0 | *** |
| | 1:1 | Yellow | 8 | 91 | 1 | *** |
| | 10:1 | Yellow | 37 | 62 | 1 | *** |
| TML90-11:EA213 | 1:1 | Yellow | 6 | 86 | 8 | *** |
| | 10:1 | Yellow | 25 | 70 | 5 | *** |
| TML54:EA213 | 1:10 | Yellow | 0 | 100 | 0 | *** |
| | 1:1 | Yellow | 0 | 100 | 0 | *** |
| | 10:1 | Yellow | 0 | 96 | 4 | *** |
| TML54-15:EA213 | 1:1 | Yellow | 0 | 100 | 0 | *** |
| | 10:1 | Yellow | 0 | 96 | 4 | *** |
| TML125:EA213 | 1:10 | Yellow | 0 | 100 | 0 | *** |
| | 1:1 | Yellow | 5 | 95 | 0 | *** |
| | 10:1 | Yellow | 13 | 87 | 0 | *** |
| TML41:EA213 | 1:10 | Yellow | 2 | 98 | 0 | *** |
| | 1:1 | Yellow | 0 | 100 | 0 | *** |
| | 10:1 | Yellow | 38 | 56 | 6 | *** |
| TML89:EA213 | 1:10 | Yellow | 9 | 86 | 5 | NS |

TABLE 1-continued

Competition Studies With Comp⁻ Mutants and Transconjugants

| Strains Fix+:Fix− | Input Ratio Fix+:Fix− | Plant Color | % Nodules Formed by | | | Significance[a] |
|---|---|---|---|---|---|---|
| | | | Fix+ | Fix− | Both | |
| | 1:1 | Green | 51 | 46 | 3 | NS |
| | 10:1 | Green | 88 | 7 | 3 | NS |

[a] A chi-square analysis was used to test the deviation of the results from the expected ratio (1:1, 10:1 and 1:10) for the single strain:single strain nodules (df = 1);
NS — not significant;
***P > 0.005.

TABLE 2

Percentage Recovery of Comp⁻ Mutants on the Cultivar Peking

| Strain | Inoculum Level[1] | Occupancy[2] |
|---|---|---|
| USDA257 | $40 \times 10^8$ | 97% |
| TML89 | $4 \times 10^8$ | 97% |
| TML90 | $40 \times 10^8$ | 42% |
| TML41 | $3 \times 10^8$ | 22% |
| TML125 | $4 \times 10^8$ | 18% |
| TML54 | $40 \times 10^8$ | 4% |

[1] cells per 2.5 cm of a row.
[2] The least significant different (LSD) at the 0.05 level was 37%.

I claim:

1. A method for separating a collection of one or more test Rhizobium strains into a Comp$^{above}$ collection and a Comp$^{below}$ collection, comprising in sequence the steps of:
   (a) inoculating a first legume plant with a mixture of a Fix+ test Rhizobium strain and a Fix− reference Rhizobium strain, wherein the test and reference strains are both Nod+ on the plant, and the reference strain does not produce a phytotoxin;
   (b) growing the plant for a time sufficient for an uninoculated plant of the same variety grown under the same conditions to be yellow due to nitrogen deficiency; and
   (c) identifying the strain to be Comp$^{above}$ if the plant is green due to nitrogen sufficiency or to be Comp$^{below}$ if the plant is yellow due to nitrogen deficiency, wherein the Comp$^{above}$ and Comp$^{below}$ phenotypes are respectively more or less competitive than a Comp criterion, the criterion being measured relative to the reference strain;

whereby the test strain's Comp phenotype relative to the Comp criterion is determined.

2. A method according to claim 1, wherein the Fix− phenotype results from a nif− genotype.

3. A method according to claim 1, wherein the plant is of the genus Glycine and the test and reference strain is *Rhizobium fredii*.

4. A method according to claim 1, wherein the plant is of the genus Glycine and the test and reference strain is *Bradyrhizobium japonicum*.

5. A method according to claim 4, wherein the reference strain is EA213.

6. A method according to claim 4, wherein the soybean is of the variety Peking.

7. A method according to claim 1, wherein the mixture has an input ratio about ten or less than a factor of ten from a multiple-strain transition ratio.

8. A method according to claim 1, wherein the mixture has an input ratio greater than a factor of ten from a multiple-strain transition ratio.

9. A method according to claim 1, wherein the mixture has an input ratio above a multiple-strain transition ratio, whereby a Comp$^{above}$ strain may be separated from among several Comp$^{below}$ strains.

10. A method according to claim 1, wherein the mixture has an input ratio below a multiple-strain transition ratio, whereby a Comp$^{below}$ strain may be separated from among several Comp$^{above}$ strains.

11. A method according to claim 1, further comprising the steps of inoculating and observing a second legume plant essentially as described in claim 1, wherein the first and second plants are of the same species and variety, and wherein the plants are inoculated with mixtures having different input ratios.

12. A method according to claim 11, wherein the mixtures inoculating the first and second plants have input ratios differing by less than or about a factor of one hundred.

13. A method according to claim 12 wherein the mixtures inoculating the first and second plants have input ratios differing by about a factor of ten.

14. A method according to claim 1, wherein the plant is grown in a support comprising soil.

15. A method according to claim 1, wherein the plant is grown in a substrate comprising artificial materials.

16. A method according to claim 15, wherein the artificial materials comprise vermiculite.

17. A method according to claim 1, wherein the test strain is a natural isolate.

18. A method according to claim 1, wherein the test strain comprises inserted DNA.

19. A method according to claim 18, wherein the inserted DNA is a transposon.

20. A method according to claim 19, wherein the transposon is Tn5.

21. A method according to claim 18, wherein the inserted DNA comprises Rhizobium DNA.

22. A method according to claim 1, further comprising, after step (c), the step of:
   (d) determining the nodule occupancy rates for the test and reference strains; whereby the test strain's Comp phenotype is confirmed.

* * * * *